United States Patent [19]

Covey et al.

[11] Patent Number: 4,839,349

[45] Date of Patent: Jun. 13, 1989

[54] PHOSPHORUS SUBSTITUTED TETRAZOLINONES AND PESTICIDAL USE

[75] Inventors: Rupert A. Covey, Bethany; Richard C. Moore, Wallingford, both of Conn.

[73] Assignee: Uniroyal Chemical Company, Inc., Middlebury, Conn.

[21] Appl. No.: 202,071

[22] Filed: Jun. 3, 1988

[51] Int. Cl.[4] .......................... A01N 57/32; C07F 9/65
[52] U.S. Cl. ......................................... 514/92; 548/111
[58] Field of Search ........................... 548/111; 514/92

[56] References Cited

U.S. PATENT DOCUMENTS

| | | | |
|---|---|---|---|
| 3,523,951 | 8/1970 | Rufenacht | 260/306.7 |
| 3,661,926 | 5/1972 | Van Den Bos et al. | 260/307 A |
| 3,780,053 | 12/1973 | Miesel | 260/308 C |
| 3,973,010 | 8/1976 | Dawes et al. | 424/200 |
| 4,211,703 | 7/1980 | Berges | 548/112 |
| 4,426,379 | 1/1984 | Edwards | 548/111 |
| 4,590,182 | 5/1986 | Haga et al. | 548/111 |
| 4,618,365 | 10/1986 | Covey et al. | 71/92 |
| 4,645,761 | 2/1987 | Haga et al. | 548/111 |
| 4,734,124 | 3/1988 | Chang et al. | 544/105 |

FOREIGN PATENT DOCUMENTS

| | | |
|---|---|---|
| 65216 | 11/1982 | European Pat. Off. |
| 2527676 | 1/1977 | Fed. Rep. of Germany . |
| 3126390 | 1/1983 | Fed. Rep. of Germany . |
| 149298 | 9/1982 | Japan . |
| 932388 | 7/1963 | United Kingdom . |

OTHER PUBLICATIONS

Tsuge et al., J. Org. Chem. 45, 5130 (1980).
Horwitz et al., J. Am. Chem. Soc. 81, 3076 (1959).
Vandensavel et al., J. Org. Chem., 88, 675 (1973).

Primary Examiner—Richard L. Raymond
Attorney, Agent, or Firm—Raymond D. Thompson

[57] ABSTRACT

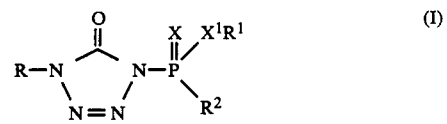

where X is oxygen or sulfur; $X^1$ is oxygen, sulfur, NH or $NR^3$; $C_1$-$C_{12}$ alkyl, $C_2$-$C_{13}$ alkoxyalkyl, $C_7$-$C_9$ aralkyl, $C_{5-6}$ cycloalkyl, $C_3$-$C_{12}$ alkenyl, naphthyl, phenyl, phenyl substituted with at least one member selected from the group consisting of: halogen, $C_1$-$C_4$ alkyl, $C_1$-$C_4$ alkoxy, methylenedioxy, $NR^4R^5$ (wherein $R^4$ and $R^5$ are the same or different and are hydrogen or $C_1$-$C_6$ alkyl), $C_2$-$C_5$ alkoxycarbonyl, carboxy, phenoxy, nitro, cyano, trihalomethyl, trihalomethoxy, $C_1$-$C_6$ alkylthio, and $C_1$-$C_6$ fluoroalkylthio; or benzyl substuted with at least one member selected from the group consisting of: halogen $C_1$-$C_4$ alkyl, $C_1$-$C_4$ alkoxy, methylenedioxy, $C_2$-$C_5$ alkoxycarbonyl, phenoxy, nitro, cyano, trihalomethyl, trihalomethoxy, $C_1$-$C_6$ alkylthio and $C_1$-$C_6$ fluoroalkylthio; and $R^1$, and $R^3$ may be the same or different and are $C_1$-$C_4$ alkyl and $R_2$ may be $C_1$-$C_4$ alkyl, alkoxy, alkylthio and alkyl amino is disclosed.

The application is also directed to a pesticidal composition comprising the above-recited compound and a carrier.

14 Claims, No Drawings

PHOSPHORUS SUBSTITUTED TETRAZOLINONES AND PESTICIDAL USE

FIELD OF THE INVENTION

This invention is directed to novel organophosphorous-substituted tetrazolinones, which compounds exhibit unexpectedly desirable activity as insecticides, including as soil-applied insecticides, and as acaricides and nematicides. In other aspects, this invention is directed to pesticidal compositions comprising such compounds as well as to methods of controlling insects, acarids and nematodes employing such compositions.

BACKGROUND OF THE INVENTION

The destruction by nematodes (especially by so-called root-knot nematodes), acarids and insects presents a serious problem to agriculture. A wide variety of field crops are in need of protection from nematodes, acarids and/or insects including such valuable crops as soybeans, corn, peanuts, cotton, alfalfa and tobacco. In addition, vegetables, such as tomatoes, potatoes, sugarbeet, carrots and the like as well as fruits, nuts, ornamentals and seed bed crops such as apples, peaches, peas, citrus fruit and grapes may also require protection from the ravages of such pests.

One particularly difficult type of insect to control are those which, at one or more stage of their life, inhabit the soil and cause destruction to the roots of agriculturally valuable plants. Representative of this type of insect is the corn rootworm.

Corn rootworms are the larvae of several species of beetles of the genus Diabrotica. These larvae cause severe damage to the roots of corn plants, particularly in fields where one corn crop follows another in successive seasons. The adult beetles lay their eggs in the soil of a maturing corn crop. The eggs lay dormant in the soil until the following spring. Then they hatch in response to favorable soil temperatures and the larvae feed on the roots of young corn plants causing reduction in yield and/or the stalks to topple over when subjected to either wind or wet soil conditions. The fallen stalks cannot be satisfactorily harvested by mechanical harvesters causing significant losses.

Control of such soil-dwelling insects and nematodes is difficult in that most organophosphorous-type insecticidal and nematicidal compounds have an undesirably short residual life in soil. Accordingly, it is completely unexpected that the novel organophosphorous-substituted tetrazolinone compounds of this invention exhibit desirable foliar insecticidal and acaricidal properties coupled with admirable control of soil-dwelling insects and nematodes.

U.S. Pat. No. 3,523,951 (Rufenacht) Aug. 11, 1970, discloses 1,3,4-thiadiazole-5(4H)-one derivatives having fungicidal, insecticidal and nematocidal properties.

U.S. Pat. No. 3,661,926 (Van Den Bos et al) May 9, 1972, discloses 5-substituted-1,3,4-oxadiazolone (2) derivatives of phosphoric acid and thiophosphoric acid useful as insecticides and acaracides.

U.S. Pat. No. 4,426,379 (Edwards) Jan. 17, 1984, discloses 2-oxo-3-dialkoxyphosphoro-5-cyclopropyl-1,3-4-oxadiazoline useful as insecticides.

U.S. Pat. No. 4,618,365 (Covey et al) Oct. 21, 1986 discloses substituted tetrazolinones carrying carbamyl moieties useful as herbicides.

U.S. Pat. No. 3,780,053 to Miesel shows a class of 5-oxo(thioxo)-1,3-(alkyl, alkenyl or cycloalkyl)-1,2,4-triazolin-4-yl methyl phosphorous derivatives having insecticidal, acaricidal and antihelminthic activity.

Japanese Patent No. 1982-14929 to Matsui et al shows certain phosphorothiomethyl-substituted triazolinones which exhibit insecticidal and acaricidal activity.

U.S. Pat. No. 3,973,010 to Dawes et al shows a class of triazolyl phosphoric esters having insecticidal and acaricidal activity.

U.S. Pat. No. 4,211,703 to Berges shows certain phosphoroalkyl and esterified phosphoroalkyl substituted tetrazole thioazoles useful as intermediates in the preparation of certain antibiotics.

European Patent 65,216 to Kubel et al shows certain 5-(1,2,4-triazol-5-ylmethyl)(di)thiophosphonate derivatives having insecticidal, acaricidal, nematicidal and fungicidal activity.

German Offenlegungsschrift No. 25 27 676 shows a class of 5-triazolylmethyl thiophosph(on)ates useful as insecticides, acaricides and nematicides.

British Pat. No. 932,388 to Sherlock shows certain heterocyclic thiophosphoric acid esters exhibiting acaricidal activity.

Tsuge et al, J. Org. Chem. 45, 5130 (1980); Horwitz et al, J. Am. Chem. Soc. 81, 3076 (1959); and Vandensavel et al, J. Org. Chem., 88, 675 (1973) all show processes for the production of tetrazolinones.

Substituted tetrazoline compounds carrying thiophosphoric acid ester moieties as substituents are known as pesticides, as disclosed in British Pat. No. 932,388 (Sherlock) July 24, 1963 and Ger. Offen. No. DE 3,126,390 (Maer et al) Jan. 13, 1983.

In the case of Sherlock, the thiophosphoric acid ester moiety is attached to the carbon atom of the heterocyclic ring rather than to a nitrogen atom, unlike Mauer et al. In both cases they are not tetrazolinones. They do not have C=O in the ring. Additionally, the compounds of Sherlock and Mauer et al are thiophosphoric acid esters while the compounds of the instant invention are phosphates, i.e., phosphorus attached directly to the nitrogen of the tetrazolinone ring.

U.S. Pat. No. 4,734,124 discloses the herbicidal utility of certain tetrazolinones which do not contain any phosphorous linkage to the tetrazolinone structure. This is functionally different than the compounds of our invention.

U.S. Pat. Nos. 4,590,182 and 4,645,761 disclose certain organophosphorous compounds as insecticidal, miticidal or nematicidal. These compounds contain no tetrazolinone moiety in their respective structures.

However, while certain of the above-listed publications disclose pesticidally active compounds, it would nevertheless be desirable to possess compounds which exhibited enhanced control of pests particularly of soil-dwelling insects.

Accordingly, it is an object of this invention to provide novel compounds, exhibiting unexpectedly desirable pesticidal activity.

It is a further object of this invention to provide novel compounds exhibiting admirable activity against soil dwelling insects.

It is another object of this invention to provide pesticidal compositions comprising such novel compounds.

It is yet another object of this invention to provide methods of controlling pest employing such compositions.

The above objects, and the additional objects, will become more fully apparent from the following disclosure and accompanying Examples.

BRIEF DESCRIPTION OF THE INVENTION

In one aspect, the present claimed invention is directed to a compound having the formula:

$$R-N\underset{N=N}{\overset{\overset{O}{\|}}{\diagdown}}N-P\overset{\overset{X}{\|}}{\diagdown}\overset{X^1R^1}{\diagdown}R^2 \quad (I)$$

wherein
X is
  O, S;
$X^1$ is:
  O, S, NH or $NR^3$;
R is:
  $C_1-C_{12}$ alkyl,
  $C_2-C_{13}$ alkoxyalkyl,
  $C_7-C_9$ aralkyl,
  $C_5-C_6$ cycloalkyl
  $C_3-C_{12}$ alkenyl,
  naphthyl,
  phenyl,
  phenyl substituted with at least one member selected from the group consisting of:
    fluorine,
    chlorine,
    bromine,
    iodine,
    $C_1-C_4$ alkyl,
    $C_1-C_4$ alkoxy,
    methylenedioxy,
    $NR^4R^5$ wherein $R^4$ and $R^5$ are the same or different and are hydrogen or $C_1-C_6$ alkyl,
    $C_2-C_5$ alkoxycarbonyl,
    carboxy,
    phenoxy,
    nitro,
    cyano,
    trihalomethyl wherein halo is fluorine, chlorine or bromine,
trihalomethoxy wherein halo is fluorine, chlorine or bromine,
    $C_1-C_6$ alkylthio, and
    $C_1-C_6$ fluoroalkylthio;
  benzyl substituted with at least one member selected from the group consisting of:
    fluorine,
    chlorine,
    bromine
    iodine,
    $C_1-C_4$ alkyl,
    $C_1-C_4$ alkoxy,
    methylenedioxy,
    $C_2-C_5$ alkoxycarbonyl,
    phenoxy,
    nitro,
    cyano,
    trihalomethyl wherein halo is fluorine, chlorine or bromine,
    trihalomethoxy wherein halo is fluorine, chlorine or bromine,
    $C_1-C_6$ alkylthio, and
    $C_1-C_6$ fluoroalkylthio;

$R^1$, and $R^3$ may be the same or different and are
  $C_1-C_4$ alkyl; and
$R^2$ is $C_1-C_4$ alkyl,
  $C_1-C_4$ alkoxy,
  $C_1-C_4$ alkylthio,
  $C_1-C_4$ alkylamino.

DETAILED DESCRIPTION OF THE INVENTION

The composition of this invention is comprised of (A) a compound having a structure within that of formula (I) above and (B) a suitable carrier. Such suitable carriers may be solid or liquid in nature.

Suitable liquid carriers may be comprised of water, alcohols, ketones, phenols, toluene and xylenes. In such formulations, additives conventionally employed in the art may be utilized such as, for example, one or more surface active agents and/or inert diluents, to facilitate handling an application of the resulting pesticide composition.

The pesticidal compositions may alternatively comprise solid carriers taking the form of dusts, granules, wettable powders, pastes, aerosols, emulsions, emulsifiable concentrates, and water-soluble solids.

For example, the pesticidal compounds of this invention may be applied as dusts when admixed with or absorbed onto powdered solid carriers, such as mineral silicates, e.g., mica, talc, pyrophyllite and clays, together with a surface-active dispersing agent so that a wettable powder is obtained which then is applicable directly to the loci to be treated. Alternatively, the powdered solid carrier containing the compound admixed therewith may be dispersed in water to form a suspension for application in such form.

Granular formulations of the compounds, suitable for application by broadcasting, side dressing, soil incorporation or seed treatment, are suitably prepared using a granular or pellitized form of carrier such as granular clays, vermiculite, charcoal or corn cobs.

Alternatively, the pesticidal compounds may be applied in liquids or sprays when utilized in a liquid carrier, such as in a solution comprising a compatible solvent such as acetone, benzene, toluene or kerosene, or as dispersed in a suitable non-solvent medium, for example, water.

Another method of application to loci to be treated is aerosol treatment, for which the compound may be dissolved in an aerosol carrier which is a liquid under pressure but which is a gas at ordinary temperature (e.g., 20° C.) and atmospheric pressure. Aerosol formulations may also be prepared by first dissolving the compound in a less volatile solvent and then admixing the resulting solution with a highly volatile liquid aerosol carrier.

For pesticidal treatment of plants (such term including plant parts), the compounds of the invention preferably are applied in aqueous emulsions containing a surface-active dispersing agent which may be non-ionic, cationic or anionic. Suitable surface-active agents include those known in the art, such as those disclosed in U.S. Pat. No. 2,547,724 (columns 3 and 4). The compounds of the invention may be mixed with such surface-active dispersing agents, with or without an organic solvent, as concentrates for the subsequent addition of water to yield aqueous suspensions of the compounds at desired concentration levels.

In addition, the compounds may be employed with carriers which themselves are pesticidally active, such as insecticides, acaricides, fungicides or bactericides.

It will be understood that the amount of the pesticidally active compound in a given formulation will depend upon the specific pest to be combatted, as well as upon the specific chemical composition and formulation of the compound being employed, the method of applying the compound/formulation and the locus of treatment so that the pesticidally effective amount of the compound may vary widely. Generally, however, concentrations of the compound as the active ingredient in pesticidally effective formulations may range from about 0.1 to about 95 percent by weight. Spray dilutions may be as low as a few parts per million, while at the opposite extreme, full strength concentrates of the compound may be usefully applied by ultra low volume techniques. Concentration per unit area, where plants constitute the loci of treatment, may range between about 0.01 and about 50 pounds per acre, with concentrations of between about 0.1 and about 10 pounds per acre preferably being employed for crops such as corn, tobacco, rice and the like.

To combat pests sprays of the compounds may be applied to the pests directly and/or to plants upon which they feed or nest. The pesticidally active formulations may also be applied to the soil o other medium in which the pests are present.

Harmful insects, nematodes and acarids attack a wide variety of plants, including both ornamental and agricultural plants and inflict damage by consuming roots and/or foliage, withdrawing vital juices from the plants, secreting toxins and often by transmitting diseases. The compounds of the present invention may be advantageously utilized to minimize or prevent such damage. The specific methods of application, as well as the selection and concentration of these compounds will, of course, vary depending upon such circumstances as geographic area, climate, topography, plant tolerance, etc. For specific circumstances, one skilled in the art may readily determine the proper compound, concentration and method of application by routine experimentation.

The compounds of the invention are particularly useful as insecticides, nematodes and acaricides, for foliar and/or soil application. The compounds are particularly effective for controlling insects, such as corn rootworm, which live in the soil during one or more phases of their lives, by means of soil application.

EXAMPLES

The following Examples are intended to further illustrate the invention, and are not intended to limit the scope of the invention in any manner whatsoever.

The chemicals of this invention can be prepared by using as starting materials 1-substituted-5(4H) tetrazolinones. These compounds are known and can be prepared by known procedures. For example, 1-phenyl-5(4H)-tetrazolinone can be prepared by the method of Horwitz et al, J.A.C.S. 81 3076 (1959), by reacting phenylisocyanate with sodium azide in the presence of aluminum chloride. Alternatively, it can be prepared by reacting phenyl isocyanate with trimethylsilyl azide; see Tsuge et al, J. Org. Chem. 45 5130 (1980).

The compounds of this invention may be prepared by reacting the selected 1-substituted-5(4H)-tetrazolinone having the formula (II)

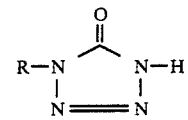

with a chlorophosphate or chlorophosphonate of the formula (III)

(where R, $R^1$, $R^2$, X and $X^1$ have the meaning given in Compound I) in the presence of a suitable acid acceptor such as pyridine, triethylamine, sodium hydroxide or potassium carbonate. This reaction is run in an inert solvent such as acetone, acetonitrile, toluene, chloroform or the like.

The chlorophosphates are widely used in the literature. They can be purchased commercially, or can be prepared by known processes, e.g. Methoden der organischen chemie (Houben-Weyl), 4th edition, Volume 12/2 (1964), pages 607–618; Thieme-Berlag, Stuttgart).

EXAMPLE 1

Preparation of 1-(phenyl)-5(4H)-tetrazolinone

Aluminum chloride (15.0 g, 0.11 mol) was added in small portions while stirring to 75 ml of tetrahydrofuran (THF, tested for absence of peroxide), keeping the temperature of the solution below 30° C. Phenyl isocyanate (11.9 g, 0.1 mole), 50 ml THF and 19.5 g, (0.3 mol) of sodium azide were combined in a separate flask, equipped with a condenser and thermometer. The aluminum chloride solution was added to the flask and the mixture was refluxed at 70° to 80° C. for 16 hours. The mixture was cooled to room temperature, and 10 ml of concentrated hydrochloric acid and 10 ml of water were added in one portion to the stirred mixture. The mixture was warmed slightly, and nitrogen was swept over the surface to remove unreacted hydrazoic acid. The mixture was stirred for 20 minutes and filtered. The salt was washed twice with 50 ml portions of THF. The THF layers were combined and after concentration under reduced pressure the product crystallized. After recrystallization from ethanol, 12.2 g (75%) of white crystals were obtained, mp 189°–190° C. dec. The structure was confirmed by infrared (IR) and nuclear magnetic resonance (NMR) analyses.

This compound was subsequently reacted with diethylchlorothiophosphate resulting in Compound No. 5 of Table I.

EXAMPLE 2

Preparation of 1-methyl-4-(diethoxythio-phosphoro)-5(4H)tetrazolinone (Compound No. 1)

1-Methyl-5(4H)-tetrazolinone (2.00 g, 0.02 mol.) was dissolved in 20 ml of acetonitrile. Anhydrous potassium carbonate (5.25 g, 0.04 mol.) was heated to reflux for 1 hour (80° C.). The mixture was cooled to 25° C. and 3.77 g (0.02 mol.) of diethylchlorothiophosphate in 10 ml of acetonitrile was added dropwise during 10 minutes. There as no exotherm, but a precipitate of potassium chloride formed. The mixture was refluxed for 1 hour, cooled and suction filtered to remove precipitated salts. The solvent was removed with a rotary evaporator leaving a clear yellow oil, weight 4.20 g (83%).

The structure was confirmed by Mass Spectrometry, IR and NMR spectra.

EXAMPLE 3 tion of their key structural configuration and functional groups. The analytical determinations were substantially confirmed by nuclear magnetic resonance and infrared methods. Table II sets forth nomenclature for the compounds 1-13. These compounds and their NMR spectra are listed in Table I. In such table; s=singlet; d=doublet; t=triplet; q=quartet; and m=multiplet.

TABLE I

| Cpd. No. | R | $R^1$ | $R^2$ | X | $X^1$ | State | Nuclear Magnetic Resonance (NMR) Data (ppm, $CDCl_3$) |
|---|---|---|---|---|---|---|---|
| 1 | $CH_3$ | $C_2H_5$ | $C_2H_5O$ | S | O | Oil | 1.40 (2t,6H), 3.55 (S,3H), 3.87-4.47 (2q,4H) |
| 2 | n-$C_3H_7$ | " | " | " | " | Oil | 0.96 (t,3H), 1.40 (2t,6H), 1.90 (m,2H), 3.82 (t,2H) 4.10-4.49 (2q,4H) |
| 3 | $C_2H_5$ | " | " | " | " | Oil | 1.43 (3t,9H), 3.7-4.7 (3q,6H) |
| 4 | $(CH_3)_2(CH)$ | " | " | " | " | Oil | 1.42, 1.53 (2d,2t,12H), 4.1-4.6 (2q,1m,5H) |
| 5 | $C_6H_5$ | " | " | " | " | Soft Solid | 1.42, (2t,6H), 4.0-4.6 (m,4H), 7.3-7.9 (m,5H) |
| 6 | $(CH_3)_3C$ | " | " | " | " | Oil | 1.3-1.8, (2t,6H; S,9H), 4.40 (2q,4H) |
| 7 | $CH_2=CHCH_2$ | " | " | " | " | Oil | 1.38 (2t,6H), 4.39 (2q,4H), 4.6-6.1 (M,5H) |
| 8 | $C_6H_{10}$ | " | " | " | " | Oil | 1.40 (2t,6H), 1.4-2.1 (m,10H), 4.1-4.7 (2q,m,5H) |
| 9 | 2Cl—$C_6H_4$ | " | " | " | " | Oil | 1.42 (2t,6H), 4.37 (2q,4H), 7.45 (m,4H) |
| 10 | 3-Cl—$C_6H_4$ | " | " | " | " | Soft Cream Solid | 1.40 (2t,6H), 3.8-4.7 (2q,4H), 7.3-8.0 (m,4H) |
| 11 | 4-Cl—$C_6$—$H_4$ | " | " | " | " | Soft Orange Solid | 1.43 (2t,6H), 4.0-4.8 (2q,4H), 7.64 (m,4H) |
| 12 | 4-$CH_3$—$C_6$—$H_4$ | " | " | " | " | Soft Cream Solid | 1.36 (2t,6H), 2.36 (S,3H), 4.30 (2q,4H), 7.52 (m,4H) |
| 13 | 2-$SCH_3$—$C_6H_4$ | " | " | " | " | Oil | 1.43 (2t,6H), 2.42 (S,3H), 4.34 (2q,4H), 7.32 (m,4H) |
| 14 | 4-$NO_2$—$C_6H_4$ | " | " | " | " | Yellow Semi-Solid | 1.32 (2t,6H), 4.15 (2q,4H), 8.23 (m,4H) |
| 15 | 3-$CF_3$—$C_6$—$H_4$ | " | " | " | " | Soft Cream Solid | 1.42 (2t,6H), 4.29 (2q,4H), 7.94 (m,4H) |
| 16 | 1-naphthyl | " | " | " | " | Oil | 1.0-1.6 (2t,6H), 3.8-4.7 (2q,4H), 7.4-8.1 (m,7H) |

TABLE II

NOMENCLATURE FOR COMPOUNDS OF INVENTION

| Cmpd. No. | | Name | |
|---|---|---|---|
| 1 | O,O—Diethyl | (4,5-dihydro-4-methyl-5-oxo-1H—tetrazol-1-yl) | phosphonothioate |
| 2 | " | (4,5-dihydro-5-oxo-4-propyl-1H—tetrazol-1-yl) | " |
| 3 | " | (4,5-dihydro-4-ethyl-5-oxo-1H—tetrazol-1-yl) | " |
| 4 | " | [(4,5-dihydro-4-(1-methylethyl)5-oxo-1H—tetrazol-1-yl] | " |
| 5 | " | (4,5-dihydro-5-oxo-4-phenyl-1H—tetrazol-1-yl) | " |
| 6 | " | [(4,5-dihydro-4-(1,1-dimethylethyl)5-oxo-1H—tetrazol-1-yl] | " |
| 7 | " | [(4,5-dihydro-5-oxo-2-(propenyl)-1H—tetrazol-1-yl] | " |
| 8 | " | (4-cyclohexyl-4,5-dihydro-5-oxo-1H—tetrazol-1-yl) | " |
| 9 | " | [4-(2-chlorophenyl)-4,5-dihydro-5-oxo-1H—tetrazol-1-yl] | " |
| 10 | " | [4-(3-chlorophenyl)-4,5-dihydro-5-oxo-1H—tetrazol-1-yl] | " |
| 11 | " | [4-(4-chlorophenyl)4,5-dihydro-5-oxo-1H—tetrazol-1-yl] | " |
| 12 | " | [4,5-dihydro-4(4-methylphenyl)-5-oxo-1H—tetrazol-1-yl] | " |
| 13 | " | [4,5-dihydro-4-(2-methylthiophenyl)-5-oxo-1H—tetrazol-1-yl] | " |
| 14 | " | [4,5-dihydro-4-(4-nitrophenyl)-5-oxo-1H—tetrazol-1-yl] | " |
| 15 | " | [4,5-dihydro-5-oxo-4-(3-trifluoromethylphenyl)1H—tetrazol-1-yl] | " |
| 16 | " | [4,5-dihydro-4-(1-naphthyl)-5-oxo-1H—tetrazol-1-yl] | " |

Preparation of 1-(2-methylthiophenyl)-4-(diethoxythiophosphoro)-5(4H-tetrazolinone Compound No. 13)

A solution of 2-(methylthiophenyl)-5(4H)tetrazolinone (3.12 g, 0.015 mol) in 20 ml of acetonitrile was combined with 4.83 g, 0.035 mol) of anhydrous potassium carbonate, and the mixture was refluxed for 1 hour. The mixture was cooled to 20° C. and 3.39 g (0.018 mol) of diethylchlorothiophosphate in 10 ml of acetonitrile was added dropwise. The mixture was then heated to boiling for 2 hours, whereupon infrared analysis indicated that the reaction was complete. The mixture was cooled and filtered with use of Celite (filter acid). The solvent was removed, leaving 5.1 g. (94%) of amber oil.

The structure was confirmed by Mass Spectrometry, IR and NMR spectra.

EXAMPLE 4

Compounds No. 2-12, 14-16

Additional compounds were prepared applying essentially the experimental approach previously described. The compounds were analyzed for determina- The pesticide of this invention may be applied to the soil in forms well known to the art such as a solution in a suitable solvent such as aliphatic alcohols, aliphatic ketones, and the like, or as a wettable powder or an emulsifiable concentrate. Dust and granular forms may also be employed; pesticide in a granular form is usually preferred for field treatment. In the latter case, the pesticide is dissolved in a solvent and sprayed onto an inert mineral carrier such as attapulgite granules (10-100 mesh), and the solvent is then evaporated. Such granular compositions may contain from 2-25% pesticide based on carrier plus pesticide, usually 3-15%. In addition, the pesticide may also be incorporated into a polymeric carrier such as polyethylene, polypropylene, butadiene-styrene, styrene-acrylonitrile resins, polyamides, poly(vinyl acetates) and the like. When encapsulated the pesticide may advantageously be released over an even longer time period, extending its effectiveness further than when used in non-encapsulated form.

In order to carry out this invention the pesticide is applied to the soil at a rate of from 0.25-12 lbs./a (0.28-13.4 kg/ha). However, it should be considered that in so-called "band" applications, i.e., when the pesticide is placed on or into the soil along with seeds as a band approximately 2-8 inches (5-20 cm) on each side of the row of seeds, lower rates such as 0.25-3 lbs/a (0.28-3.4 kg/ha) may suffice to control corn worm. When the pesticide of this invention is spread in a so-called "broadcast" fashion, larger doses may be required, such as 1-12 lbs/a (1.12-13.4 kg/ha).

It is also within the contemplation of this invention that the pesticide be added to the soil in combination with other pesticides, as well as plant nutrients, fertilizers and the like.

EXAMPLE 5

Preparation of Formulations

The remaining examples relate to the pesticidal use of the compounds of this invention. In all these examples the compounds were diluted to one of the following concentrations: 500 or 40 parts per million (ppm). To accomplish these dilutions, 0.05 g of the compound in questions was dissolved in 10 ml of acetone to which were added 4 drops of a suitable wetting agent. This solution was further diluted with 100 ml of water to provide a 500 ppm suspension. In a similar manner the still more dilute suspension of 40 ppm was prepared.

All the tests discussed below, which involved treatment with compounds of this invention at concentrations of 500 and 40 ppm were always repeated with controls, in which the active compound was not provided, to permit a comparison upon which the percent control was calculated.

EXAMPLE 6

Southern Corn Rootworm Test

Test formulations of compounds 1-at concentration of 500 ppm of the compounds were used. Two ml of the suspension was pipetted onto a filter paper, inserted into a petri dish. Two corn seedlings were also soaked in the chemical preparation and placed in the petri dish. Dishes were held for 18 hours before being loaded with 5 corn rootworm, *Diabrotica undecimpunctata*, larvae. After six days, the number of live larvae were noted and the percent control was calculated. The results appear in Table III below.

EXAMPLE 7

Control of Southern Corn Rootworm in Soil

Test compounds were prepared at 40 ppm concentration. Two sets of plastic pots, each pot holding 330 g of soil, were drenched with 30 ml of the suspensions to give a resultant soil concentration of 4 ppm.

All experiments were conducted with 4 replicates each, including controls which have not been treated with soil insecticide. Two corn seeds were planted in each pot. One week after planting, each pot was loaded with ten corn rootworm larvae. One week after loading, scoring was undertaken by emptying the pots of their soil, filtering the soil through a fine mesh screen, retaining the larvae present. The number of live larvae was counted, and percent control of Southern corn rootworm was calculated using Abbot's formula (see J. Economic Entomology 18, 265-267 (1925).

The results of the experiments are summarized in Table III.

TABLE III

| Cpd. No. | 500 ppm | 4 ppm (soil) |
|---|---|---|
| 1 | 100 | 100 |
| 2 | 100 | 70 |
| 3 | 100 | 97 |
| 4 | 100 | 91 |
| 5 | 100 | 100 |
| 6 | 100 | 36 |
| 7 | 100 | 64 |
| 8 | 100 | 12 |
| 9 | 100 | 100 |
| 10 | 100 | 88 |
| 11 | 100 | 52 |
| 12 | 100 | 24 |
| 13 | 100 | 84 |
| 14 | 100 | 100 |
| 15 | 100 | 100 |
| 16 | 100 | 52 |

The test results demonstrate surprising and unexpected efficacy of the compounds in controlling corn rootworm especially at very low levels of concentration in soil application. The compositions also showed good efficacy in control of other insect pests including, but not limited, to two spotted mites, root knot nematodes, rice plant hoppers, tobacco budworms and others.

It is apparent that various modifications may be made in the formulation and application of the compounds of this invention without departing from the inventive concepts as defined in the claims.

What is claimed is:

1. A compound of tetrazolinones having the structural formula (I):

$$R-N\underset{N=N}{\overset{O}{\underset{\|}{\diagdown}}}N-\overset{X}{\underset{\|}{P}}\overset{X^1R^1}{\diagdown}R^2 \qquad (I)$$

wherein
X is
  O, S;
$X^1$ is:
  O, S, NH or $NH^3$;
R is:
  $C_1$-$C_{12}$ alkyl,
  $C_2$-$C_{13}$ alkoxyalkyl,
  $C_7$-$C_9$ aralkyl,
  $C_5$-$C_6$ cycloalkyl
  $C_3$-$C_{12}$ alkenyl,
  naphthyl,
  phenyl,
  phenyl substituted with at least one member selected from the group consisting of:
    fluorine,
    chlorine,
    bromine,
    iodine,
    $C_1$-$C_4$ alkyl,
    $C_1$-$C_4$ alkoxy,
    methylenedioxy,
    $NR^4R^5$ wherein $R^4$ and $R^5$ are the same or different and are hydrogen or $C_1$-$C_6$ alkyl,
    $C_2$-$C_5$ alkoxycarbonyl,
    carboxy,
    phenoxy,
    nitro,
    cyano, trihalomethyl wherein halo is fluorine, chlorine or bromine,
trihalomethoxy wherein halo is fluorine, chlorine or bromine,
$C_1$–$C_6$ alkylthio, and
$C_1$–$C_6$ fluoroalkylthio; or
benzyl substituted with at least one member selected from the group consisting of:
fluorine,
chlorine,
bromine
iodine,
$C_1$–$C_4$ alkyl,
$C_1$–$C_4$ alkoxy,
methylenedioxy,
$C_2$–$C_5$ alkoxycarbonyl,
phenoxy,
nitro,
cyano,
trihalomethyl wherein halo is fluorine, chlorine or bromine,
trihalomethoxy wherein halo is fluorine, chlorine or bromine,
$C_1$–$C_6$ alkylthio, and
$C_1$–$C_6$ fluoroalkylthio;
$R^1$, and $R^3$ may be the same or different and are $C_1$–$C_4$ alkyl; and
$R^2$ is $C_1$–$C_4$ alkyl,
$C_1$–$C_4$ alkoxy,
$C_1$–$C_4$ alkylthio,
$C_1$–$C_4$ alkylamino.

2. A compound according to claim 1 wherein
$R^1$ and $R^2$ are $C_1$–$C_4$ alkyl
X is S
$X^1$ is O
R is $C_1$–$C_{12}$ alkyl, $C_3$–$C_{12}$ alkenyl, naphthyl, or benzyl substituted with member selected from halo, nitro, and $C_1$–$C_6$ alkylthio.

3. A compound according to claim 2 wherein
$R^1$ and $R^2$ are $C_2$ alkyl,
R is $C_1$–$C_6$ alkyl.

4. A compound according to claim 2 wherein
R is $C_1$–$C_{12}$ alkyl.

5. A compound according to claim 1 wherein said compound is selected from the group consisting of:
0,0-Diethyl(4,5-dihydro-4-methyl-5-oxo-1H-tetrazol-1-yl)phosphonothioate,
0,0-Diethyl(4,5-dihydro-5-oxo-4-propyl-1H-tetrazol-1-yl)phosphonothioate,
0,0-Diethyl(4,5-dihydro-4-ethyl-5-oxo-1H-tetrazol-1-yl)phosphonothioate,
0,0-Diethyl(4,5-dihydro-4-(1-methylethyl)5-oxo-1H-tetrazol-1-yl)phosphonothionate,
0,0-Diethyl(4,5-dihydro-5-oxo-4-phenyl-1H-tetrazol-1-yl)phosphonothioate,
0,0-Diethyl(4,5-dihydro-4-(1,1-dimethylethyl)5-oxo-1H-tetrazol-1-yl)phosphonothioate,
0,0-Diethyl(4,5-dihydro-5-oxo-4-(2-propenyl)-1H-tetrazol-1-yl)phosphonothioate,
0,0-Diethyl(4-cyclohexyl-4,5-dihydro-5-oxo-1H-tetrazol-1-yl)phosphonothioate,
0,0-Diethyl(4-(2-chlorophenyl)-4,5-dihydro-5-oxo-1H-tetrazol-1-yl)phosphonothioate,
0,0-Diethyl(4-(3-chlorophenyl)-4,5-dihydro-5-oxo-1H-tetrazol-1-yl)phosphonothioate,
0,0-Diethyl(4-(4-chlorophenyl)-4,5-dihydro-5-oxo-1H-tetrazol-1-yl)phosphonothioate,
0,0-Diethyl(4,5-dihydro-4(4-methylphenyl)-5-oxo-1H-tetrazol-1-yl)phosphonothioate,
0,0-Diethyl(4,5-dihydro-4-(2-methylthiophenyl)-5-oxo-1H-tetrazol-1-yl)phosphonothioate,
0,0-Diethyl(4,5-dihydro-4-(4-nitrophenyl)-5-oxo-1H-tetrazol-1-yl)phosphonothioate,
0,0-Diethyl(4,5-dihydro-5-oxo4-)3-trifluoromethylphenyl)1H-tetrazol-1-yl)phosphonothioate,
0,0-Diethyl(4,5-dihydro-4-(1-naphthyl)-5-oxo-1H-tetrazol-1-yl)phosphonothioate, 6. A pesticidal composition comprising a suitable carrier and a pesticidally effective amount of a compound having the formula:

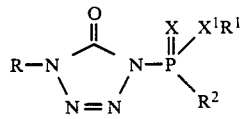

(I)

wherein
X is
O, S;
$X^1$ is:
O, S, NH or $NR^3$;
R is:
$C_1$–$C_{12}$ alkyl,
$C_2$–$C_{13}$ alkoxyalkyl,
$C_7$–$C_9$ aralkyl,
$C_5$–$C_6$ cycloalkyl,
$C_3$–$C_{12}$ alkenyl,
naphthyl,
phenyl,
phenyl substituted with at least one member selected from the group consisting of:
fluorine,
chlorine,
bromine,
iodine,
$C_1$–$C_4$ alkyl,
$C_1$–$C_4$ alkoxy,
methylenedioxy,
$NR^4R^5$ wherein $R^4$ $R^5$ are the same or different and are hydrogen or $C_1$–$C_6$ alkyl,
$C_2$–$C_5$ alkoxycarbonyl,
carboxy,
phenoxy,
nitro,
cyano,
trihalomethyl wherein halo is fluorine, chlorine or bromine,
trihalomethoxy wherein halo is fluorine, chlorine or bromine,
$C_1$–$C_6$ alkylthio, and
$C_1$–$C_6$ fluoroalkylthio; or
benzyl substituted with at least one member selected from the group consisting of:
fluorine,
chlorine,
bromine
iodine,
$C_1$–$C_4$ alkyl,
$C_1$–$C_4$ alkoxy,
methylenedioxy,
$C_2$–$C_5$ alkoxycarbonyl,
phenoxy,
nitro,
cyano, trihalomethyl wherein halo is fluorine, chlorine or bromine,
trihalomethoxy wherein halo is fluorine, chlorine or bromine,
$C_1$-$C_6$ alkylthio, and
$C_1$-$C_6$ fluoroalkylthio;

$R^1$, and $R^3$ may be the same or different and are $C_1$-$C_4$ alkyl; and $R^2$ is $C_1$-$C_4$ alkyl, $C_1$-$C_4$ alkoxy, $C_1$-$C_4$ alkylthio, $C_1$-$C_4$ alkylamino.

7. The pesticidal composition according to claim 6 wherein said compound has
$R^1$ and $R^2$ are $C_1$-$C_4$ alkyl
X is S
$X^1$ is O
R is $C_1$-$C_{12}$ alkyl, $C_3$-$C_{12}$ alkenyl, naphthyl, or benzyl substituted with member selected from halo, nitro, and $C_1$-$C_6$ alkyl thio.

8. The pesticidal composition according to claim 6 wherein said compound has
$R^1$ and $R^2$ are $C_2$ alkyl,
R is $C_1$-$C_6$ alkyl.

9. The pesticidal composition according to claim 6 wherein said compound has
R is $C_1$-$C_{12}$ alkyl.

10. The pesticidal composition according to claim 6 wherein said compound is selected from the group consisting of
O,O-Diethyl(4,5-dihydro-4-methyl-5-oxo-1H-tetrazol-1-yl)phosphonothioate,
O,O-Diethyl(4,5-dihydro-5-oxo-4-propyl-1H-tetrazol-1-yl)phosphonothioate,
O,O-Diethyl(4,5-dihydro-4-ethyl-5-oxo-1H-tetrazol-1-yl)phosphonothioate,
O,O-Diethyl(4,5-dihydro-4-(1-methylethyl)5-oxo-1H-tetrazol-1-yl)phosphonothioate,
O,O-Diethyl(4,5-dihydro-5-oxo-4-phenyl-1H-tetrazol-1-yl) phosphonothioate,
O,O-Diethyl(4,5-dihydro-4-(1,1-dimethylethyl)5-oxo-1H-tetrazol-1-yl)phosphonothioate,
O,O-Diethyl(4,5-dihydro-5-oxo-4-(2-propenyl)-1H-tetrazol-1-yl)phosphonothioate,
O,O-Diethyl(4-cyclohexyl-4,5-dihydro-5-oxo-1H-tetrazol-1-yl)phosphonothioate,
O,O-Diethyl(4-(2-chlorophenyl)-4,5-dihydro-5-oxo-1H-tetrazol-1-yl)phosphonothioate,
O,O-Diethyl(4-(3-chlorophenyl)-4,5-dihydro-5-oxo-1H-tetrazol-1-yl)phosphonothioate,
O,O-Diethyl(4-(4-chlorophenyl)-4,5-dihydro-5-oxo-1H-tetrazol-1-yl)phosphonothioate,
O,O-Diethyl(4,5-dihydro-4(4-methylphenyl)-5-oxo-1H-tetrazol-1-yl)phosphonothioate,
O,O-Diethyl(4,5-dihydro-4-(2-methylthiophenyl)-5-oxo-1H-tetrazol-1-yl)phosphonothioate,
O,O-Diethyl(4,5-dihydro-4-(4-nitrophenyl)-5-oxo-1H-tetrazol-1-yl)phosphonothioate,
O,O-Diethyl(4,5-dihydro-5-oxo4-)3-trifluoromethylphenyl)1H-tetrazol-1-yl)phosphonothioate,
O,O-Diethyl(4,5-dihydro-4-(1-naphthyl)-5-oxo-1H-tetrazol-1-yl)phosphonothioate.

11. A method of controlling insects comprising applying the to the locus to be protected an insecticidally effective amount of a compound having the formula:

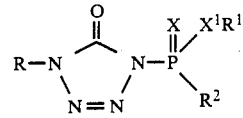

wherein
X is
O, S;
$X^1$ is:
O, S, NH or $NR^3$;
R is:
$C_1$-$C_{12}$ alkyl,
$C_2$-$C_{13}$ alkoxyalkyl,
$C_7$-$C_9$ aralkyl,
$C_5$-$C_6$ cycloalkyl
$C_3$-$C_{12}$ alkenyl,
naphthyl,
phenyl,
phenyl substituted with at least one member selected from the group consisting of:
fluorine,
chlorine,
bromine,
iodine,
$C_1$-$C_4$ alkyl,
$C_1$-$C_4$ alkoxy,
methylenedioxy,
$NR^4R^5$ wherein $R^4$ and $R^5$ are the same or different and are hydrogen or $C_1$-$C_6$ alkyl,
$C_2$-$C_5$ alkoxycarbonyl,
carboxy,
phenoxy,
nitro,
cyano,
trihalomethyl wherein halo is fluorine, chlorine or bromine,
trihalomethoxy wherein halo is fluorine, chlorine or bromine,
$C_1$-$C_6$ alkylthio, and
$C_1$-$C_6$ fluoroalkylthio; or
benzyl substituted with at least one member selected from the grou consisting of:
fluorine,
chlorine,
bromine
iodine,
$C_1$-$C_4$ alkyl,
$C_1$-$C_4$ alkoxy,
methylenedioxy,
$C_2$-$C_5$ alkoxycarbonyl,
phenoxy,
nitro,
cyano,
trihalomethyl wherein halo is fluorine, chlorine or bromine,
trihalomethoxy wherein halo is fluorine, chlorine or bromine,
$C_1$-$C_6$ alkylthio, and
$C_1$-$C_6$ fluoroalkylthio;
$R^1$, and $R^3$ may be the same or different and are $C_1$-$C_4$ alkyl; and
$R^2$ is $C_1$-$C_4$ alkyl, $C_1$-$C_4$ alkoxy, $C_1$-$C_4$ alkylthio, $C_1$-$C_4$ alkylamino.

12. A method according to claim 11 wherein said compound is applied directly to the soil.

13. A method of controlling corn rootworm comprising the application to the locus of control an effective amount of a compound of structure (I):

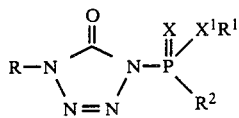

wherein
X is
O, S;
$X^1$ is:
O, S, NH or $NR^3$;
R is:
$C_1$–$C_{12}$ alkyl,
$C_2$–$C_{13}$ alkoxyalkyl,
$C_7$–$C_9$ aralkyl,
$C_5$–$C_6$ cycloalkyl
$C_3$–$C_{12}$ alkenyl,
naphthyl,
phenyl,
phenyl substituted with at least one member selected from the group consisting of:
fluorine,
chlorine,
bromine,
iodine,
$C_1$–$C_4$ alkyl,
$C_1$–$C_4$ alkoxy,
methylenedioxy,
$NR^4R^5$ wherein $R^4$ and $R^5$ are the same or different and are hydrogen or $C_1$–$C_6$ alkyl,
$C_2$–$C_5$ alkoxycarbonyl,
carboxy,
phenoxy,
nitro,
cyano,
trihalomethyl wherein halo is fluorine, chlorine or bromine,
trihalomethoxy wherein halo is fluorine, chlorine or bromine,
$C_1$–$C_6$ alkylthio, and
$C_1$–$C_6$ fluoroalkylthio; or
benzyl substituted with at least one member selected from the group consisting of:
fluorine,
chlorine,
bromine
iodine,
$C_1$–$C_4$ alkyl,
$C_1$–$C_4$ alkoxy,
methylenedioxy,
$C_2$–$C_5$ alkoxycarbonyl,
phenoxy,
nitro,
cyano,
trihalomethyl wherein halo is fluorine, chlorine or bromine,
trihalomethoxy wherein halo is fluorine, chlorine or bromine,
$C_1$–$C_6$ alkylthio, and
$C_1$–$C_6$ fluoroalkylthio;
$R^1$, and $R^3$ may be the same or different and are $C_1$–$C_4$ alkyl; and
$R^2$ is $C_1$–$C_4$ alkyl,
$C_1$–$C_4$ alkoxy,
$C_1$–$C_4$ alkylthio,
$C_1$–$C_4$ alkylamino.

14. A method of claim 13 wherein said compound of Structure I is selected from the group consisting of:
0,0-Diethyl(4,5-dihydro-4-methyl-5-oxo-1H-tetrazol-1-yl)phosphonothioate,
0,0-Diethyl(4,5-dihydro-5-oxo-4-propyl-1H-tetrazol-1-yl)phosphonothioate,
0,0-Diethyl(4,5-dihydro-4-ethyl-5-oxo-1H-tetrazol-1-yl)phosphonothioate,
0,0-Diethyl(4,5-dihydro-4-(1-methylethyl)5-oxo-1H-tetrazol-1-yl)phosphonothioate,
0,0-Diethyl(4,5-dihydro-5-oxo-4-phenyl-1H-tetrazol-1-yl)phosphonothioate,
0,0-Diethyl(4,5-dihydro-4-(1,1-dimethylethyl)5-oxo-1H-tetrazol-1-yl)phosphonothioate,
0,0-Diethyl(4,5-dihydro-5-oxo-4-(2-propenyl)-1H-tetrazol-1-yl)phosphonothioate,
0,0-Diethyl(4-cyclohexyl-4,5-dihydro-5-oxo-1H-tetrazol-1-yl)phosphonothioate,
0,0-Diethyl(4-(2-chlorophenyl)-4,5-dihydro-5-oxo-1H-tetrazol-1-yl)phosphonothioate,
0,0-Diethyl(4-(3-chlorophenyl)-4,5-dihydro-5-oxo-1H-tetrazol-1-yl)phosphonothioate,
0,0-Diethyl(4-(4-chlorophenyl)-4,5-dihydro-5-oxo-1H-tetrazol-1-yl)phosphonothioate,
0,0-Diethyl(4,5-dihydro-4(4-methylphenyl)-5-oxo-1H-tetrazol-1-yl)phosphonothioate,
0,0-Diethyl(4,5-dihydro-4-(2-methylthiophenyl)-5-oxo-1H-tetrazol-1-yl)phosphonothioate,
0,0-Diethyl(4,5-dihydro-4-(4-nitrophenyl)-5-oxo-1H-tetrazol-1-yl)phosphonothioate,
0,0-Diethyl(4,5-dihydro-5-oxo4-)3-trifluoromethylphenyl)1H-tetrazol-1-yl)phosphonothioate,
0,0-Diethyl(4,5-dihydro-4-(1-naphthyl)-5-oxo-1H-tetrazol-1-yl)phosphonothioate.

* * * * *